(12) United States Patent
Lee et al.

(10) Patent No.: US 8,703,345 B2
(45) Date of Patent: Apr. 22, 2014

(54) ELECTROLYTE INCLUDING AMIDE COMPOUND AND ELECTROCHEMICAL DEVICE INCLUDING THE SAME

(75) Inventors: Byoung-Bae Lee, Daejeon (KR); Jae-Seung Oh, Seoul (KR); Sang-Hyun Lee, Daejeon (KR); Kwon-Young Choi, Daejeon (KR); Dong-Su Kim, Daejeon (KR); Yeon-Suk Hong, Daejeon (KR); Hyo-Jin Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 71 days.

(21) Appl. No.: 13/243,178

(22) Filed: Sep. 23, 2011

(65) Prior Publication Data

US 2012/0077091 A1 Mar. 29, 2012

Related U.S. Application Data

(63) Continuation of application No. PCT/KR2011/000338, filed on Jan. 17, 2011.

(30) Foreign Application Priority Data

| Jan. 15, 2010 | (KR) | 10-2010-0003916 |
| Jan. 15, 2010 | (KR) | 10-2010-0003917 |
| Jan. 17, 2011 | (KR) | 10-2011-0004356 |

(51) Int. Cl.
*H01M 6/16* (2006.01)

(52) U.S. Cl.
USPC ........... 429/339; 429/199; 429/200; 429/341; 429/330; 252/62.2

(58) Field of Classification Search
USPC .......... 429/339, 199, 200, 341, 330; 252/62.2
See application file for complete search history.

(56) References Cited

U.S. PATENT DOCUMENTS

| 2006/0121355 A1 | 6/2006 | Kolosnitsyn et al. | |
| 2007/0042266 A1 | 2/2007 | Oh et al. | |
| 2007/0099090 A1 | 5/2007 | Oh et al. | |
| 2010/0239917 A1 | 9/2010 | Lee et al. | |
| 2010/0304222 A1* | 12/2010 | Park et al. | 429/304 |
| 2011/0014523 A1 | 1/2011 | Park et al. | |

FOREIGN PATENT DOCUMENTS

| CN | 1463455 A | 12/2003 |
| CN | 1919928 A | 2/2007 |
| JP | 2000-348760 A | 12/2000 |
| KR | 10-2007-0085575 A | 8/2007 |
| KR | 10-0751203 B1 | 8/2007 |
| KR | 10-2008-0067574 A | 7/2008 |
| KR | 10-2008-0110410 A | 12/2008 |
| KR | 10-2009-0079166 A | 7/2009 |
| KR | 10-1028887 B1 | 4/2011 |
| WO | WO 2010/101429 A2 | 9/2010 |

OTHER PUBLICATIONS

International Search Report, dated Aug. 29, 2011, issued in PCT/KR2011/000338.

* cited by examiner

*Primary Examiner* — Laura Weiner

(74) *Attorney, Agent, or Firm* — Birch, Stewart, Kolasch & Birch, LLP

(57) ABSTRACT

Disclosed is an electrolyte. The electrolyte includes an amide compound and an ionizable lithium salt. The amide compound has a specific structure in which an amine group is substituted with at least one alkoxyalkyl group and at least one halogen atom is present. The electrolyte has good thermal and chemical stability, a low resistance and a high ionic conductivity. In addition, the electrolyte has a high upper limit of electrochemical window due to its improved oxidation stability. Therefore, the electrolyte can be useful for the fabrication of an electrochemical device. Further disclosed is an electrochemical device including the electrolyte.

21 Claims, 2 Drawing Sheets

ELECTROLYTE INCLUDING AMIDE COMPOUND AND ELECTROCHEMICAL DEVICE INCLUDING THE SAME

CROSS-REFERENCE TO RELATED APPLICATION

This application a continuation of International Application No. PCT/KR2011/000338 filed Jan. 17, 2011, which claims priority under 35 U.S.C. §119(a) of Korean Patent Application Nos. 10-2010-0003916 and 10-2010-0003917 filed on Jan. 15, 2010 and No. 10-2011-0004356 filed on Jan. 17, 2011 at the Korean Intellectual Property Office, the entire contents of which are incorporated herein by reference.

TECHNICAL FIELD

The present invention relates to an electrolyte including an amide compound having a specific structure, and an electrochemical device including the electrolyte.

BACKGROUND ART

Many types of electrochemical devices, for example, lithium secondary batteries, electrolytic condensers, electric double-layer capacitors, electrochromic display devices and dye-sensitized solar cells, have been developed and are currently in use. Particularly, various researches are being done to find future practical uses of dye-sensitized solar cells. Such electrochemical devices employ various kinds of electrolytes, which are gaining more importance day by day.

Non-aqueous electrolyte solutions are presently the most widely used electrolytes. A typical non-aqueous electrolyte includes an ionizable salt such as a lithium salt, dissolved in a suitable organic solvent, such as ethylene carbonate, propylene carbonate, dimethoxyethane, γ-butyrolactone (GBL), N,N-dimethylformamide, tetrahydrofuran or acetonitrile.

However, organic solvents used in such non-aqueous electrolytes are prone to leakage due to their low viscosity and have a strong tendency to volatilize, posing a risk of evaporation. The organic solvents are highly flammable. These problems make electrochemical devices including the non-aqueous electrolytes less durable and stable.

In an effort to solve the above problems, imidazolium-based and ammonium-based ionic liquids have been proposed as electrolytes for lithium secondary batteries. However, the ionic liquids are reduced at higher voltages than the lithium ions at the anodes, or the imidazolium and ammonium cations, together with the lithium ions, are intercalated into the anodes, thus deteriorating the performance of the batteries.

Korean Patent No. 10-751203 and Korean Unexamined Patent Publication No. 10-2007-85575 disclose eutectic mixtures as electrolytes, each of which includes an amide compound and a lithium salt, wherein the amide compound is acetamide, urea, methylurea, caprolactam, valerolactam, trifluoroacetamide, carbamate, formamide or the like represented by the corresponding formula. The eutectic mixtures have relatively wide electrochemical windows and exhibit good thermal and chemical stability. Due to these advantages, the eutectic mixtures are protected from evaporating and catching fire, which are problems of conventional electrolytes arising from the use of organic solvents.

As a result, rapid development of various electrolytes is actively underway. Particularly, there is a growing need for electrolytes that contain compounds with higher thermal stability and wider electrochemical windows so as to be applicable to electrochemical devices requiring various electrochemical properties.

DISCLOSURE

Technical Problem

The present invention is designed to solve the problems of the prior art, and therefore it is an object of the present invention to provide an electrolyte that exhibits good thermal and chemical stability, and an electrochemical device including the electrolyte.

Another object of the present invention is to provide an electrolyte including a compound with low resistance in a device, and an electrochemical device including the electrolyte.

Still another object of the present invention is to provide an electrolyte that has a high upper limit of electrochemical window, a low viscosity and a high ionic conductivity while possessing good thermal stability, and an electrochemical device including the electrolyte.

Technical Solution

In order to achieve these objects, the present invention provides an electrolyte including an amide compound and an ionizable lithium salt wherein the amide compound has an amine group substituted with at least one alkoxyalkyl group and includes at least one halogen atom, represented by Formula 1:

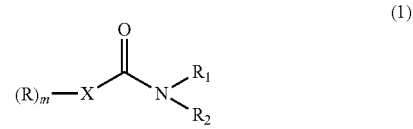

wherein R is selected from the group consisting of $C_1$-$C_{20}$ halogenated alkyl groups, halogenated alkylamine groups, halogenated alkenyl groups and halogenated aryl groups, $R_1$ and $R_2$ are each independently selected from the group consisting of hydrogen, halogen atoms, $C_1$-$C_{20}$ alkyl groups, alkylamine groups, alkenyl groups and $C_1$-$C_{20}$ aryl groups, with the proviso that at least one of $R_1$ and $R_2$ is an alkoxyalkyl group represented by $CH_3$—$(CH_2)_p$—$O(CH_2)_q$—, p being an integer from 0 to 8 and q being an integer from 1 to 8, and X is selected from the group consisting of silicon, oxygen, phosphorus, sulfur and hydrogen, provided that i) when X is hydrogen, m is 0, ii) when X is oxygen or sulfur, m is 1, iii) when X is nitrogen or phosphorus, m is 2, and iv) when X is silicon, m is 3.

As the amide compound, there may be exemplified N-methoxyethyl trifluoroethyl carbamate, N-methoxyethyl-N-methyl trifluoroethyl carbamate, N-methoxymethyl-N-methyl trifluoroethyl carbamate, N-methoxymethyl trifluoroethyl carbamate, N-methoxymethyl-N-ethyl trifluoroethyl carbamate, N-methoxyethyl-N-ethyl trifluoroethyl carbamate, N-methoxyethyl fluoroethyl carbamate, N-methoxyethyl-N-methyl fluoroethyl carbamate, N-methoxymethyl-N-methyl fluoroethyl carbamate, N-methoxymethyl fluoroethyl carbamate, N-methoxymethyl-N-ethyl fluoroethyl carbamate, N-methoxyethyl-N-ethyl fluoroethyl carbamate, N-methoxyethyl pentafluoropropyl carbamate, N-methoxyethyl-N-methyl pentafluoropropyl carbamate, N-methoxymethyl-N-methyl pentafluoropropyl carbamate, N-methoxymethyl pentafluoropropyl carbamate, N-methoxymethyl-N-ethyl pentafluoropropyl carbamate, N-methoxyethyl-N-ethyl pentafluoropropyl carbamate, N-methoxyethyl hexafluoro-2-propyl carbamate, N-methoxyethyl-N-methyl hexafluoro-2-propyl carbamate, N-methoxymethyl-N-methyl hexafluoro-2-propyl carbamate, N-methoxymethyl hexafluoro-2-propyl carbamate, N-methoxymethyl-N-ethyl hexafluoro-2-propyl carbamate, N-methoxyethyl-N-ethyl hexafluoro-2-propyl carbamate, or the like.

As the anion of the lithium salt, there may be exemplified $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, $(CF_3CF_2SO_2)_2N^-$, or the like.

The amide compound and the lithium salt are preferably present in a molar ratio of 1-8:1.

The electrolyte may have a viscosity of 200 cP or less and an electrochemical window of 0.4 to 5.0 V.

Optionally, the electrolyte may further include a carbonate. The carbonate may be any of those that are commonly used as organic solvents for electrolytes, and examples thereof include linear carbonates and cyclic carbonates. These carbonates may be used alone or as a mixture thereof. In the case where the carbonate is included, the electrolyte may have a viscosity of 50 cP or less. The viscosity of the electrolyte is preferably from 4 cP to 30 cP.

The electrolyte may be prepared into a liquid electrolyte or a solid or gel polymer electrolyte. The gel polymer electrolyte may be prepared by mixing the electrolyte of the present invention with a polymerizable monomer to obtain a precursor solution, and polymerizing the precursor solution. The polymer electrolyte may be prepared by impregnating a polymer with the electrolyte of the present invention.

Optionally, the electrolyte may further include a linear ester. Examples of linear esters suitable for use in the electrolyte include methyl propionate, ethyl propionate, propyl propionate and butyl propionate. These linear esters may be used alone or as a mixture of two or more thereof.

The electrolyte can be useful for the fabrication of an electrochemical device, such as a lithium secondary battery.

Advantageous Effects

The electrolyte of the present invention offers the following effects.

First, good thermal and chemical stability of the amide compound included in the electrolyte of the present invention can protect the electrolyte from evaporating, catching fire and side reaction, which are problems of conventional electrolytes arising from the use of organic solvents.

Second, the amide compound included in the electrolyte of the present invention exhibits a high upper limit of electrochemical window and has a low viscosity and a high electrical conductivity, making the electrolyte useful for the fabrication of an electrochemical device requiring various electrochemical properties.

Third, the amide compound included in the electrolyte of the present invention exhibits good thermal stability. Therefore, the use of the electrolyte contributes to an improvement in the safety of an electrochemical device at high temperatures.

DESCRIPTION OF DRAWINGS

The accompanying drawings illustrate preferred embodiments of the invention and, together with the foregoing disclosure, serve to provide further understanding of the technical spirit of the invention. However, the present invention is not to be construed as being limited to the drawings.

BEST MODE

Figure 1:
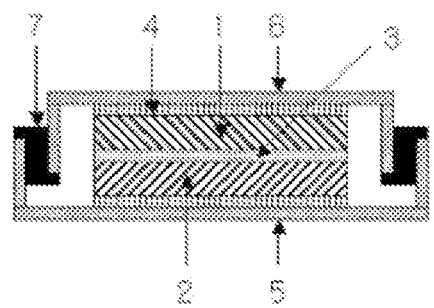
FIG. 1 is a schematic cross-sectional view of a coin-type secondary battery.

The present invention will now be described in detail. It should be understood that terms and words used in the specification and the appended claims are not to be construed as having common and dictionary meanings, but should be interpreted as having meanings and concepts corresponding to technical ideas of the present invention in view of the principle that the inventor can properly define the concepts of the terms and words in order to describe his/her own invention as best as possible.

The present invention provides an electrolyte including an amide compound and an ionizable lithium salt wherein the amide compound has an amine group substituted with at least one alkoxyalkyl group and includes at least one halogen atom, represented by Formula 1:

$$(R)_m—X \underset{}{\overset{O}{\|}} N \underset{R_2}{\overset{R_1}{\diagup}} \tag{1}$$

wherein R is selected from the group consisting of $C_1$-$C_{20}$ halogenated alkyl groups, halogenated alkylamine groups, halogenated alkenyl groups and halogenated aryl groups, $R_1$ and $R_2$ are each independently selected from the group consisting of hydrogen, halogen, $C_1$-$C_{20}$ alkyl groups, alkylamine groups, alkenyl groups and aryl groups, with the proviso that at least one of $R_1$ and $R_2$ is an alkoxyalkyl group represented by $CH_3—(CH_2)_p—O(CH_2)_q—$, p being an integer from 0 to 8 and q being an integer from 1 to 8, and X is selected from the group consisting of silicon, oxygen, phosphorus, sulfur and hydrogen, provided that i) when X is hydrogen, m is 0, ii) when X is oxygen or sulfur, m is 1, iii) when X is nitrogen or phosphorus, m is 2, and iv) when X is silicon, m is 3.

Thermal stability is a very important factor in an electrochemical device that releases a large amount of heat during use or is frequently exposed to high temperatures.

The electrolyte of the present invention exhibits superior thermal and chemical stability to organic solvents of conventional non-aqueous electrolytes. The electrolyte of the present invention exhibits superior thermal stability to eutectic mixtures of an amide compound, such as acetamide or methyl carbamate, and a lithium salt. Due to these advantages, the use of the electrolyte according to the present invention contributes to an improvement in the thermal stability of electrochemical devices. In addition, the electrolyte of the present invention can be usefully applied to electrochemical devices employing various anode materials. The presence of the halogen element in the amide compound improves the oxidation stability of the electrolyte, leading to a high upper limit of electrochemical window, and lowers the viscosity of the electrolyte, leading to improved electrical conductivity. The electrochemical window of the electrolyte according to the present invention is preferably from 0.4 to 5.0 V. The lower and upper limits in the electrochemical window range represent reduction and oxidation potentials, respectively. Particularly, the electrolyte of the present invention has a high oxidation potential. In the case where the amide compound and the lithium salt form a eutectic mixture, considerable improvements in the above-mentioned physical properties of the electrolyte are achieved.

Examples of amide compounds suitable for use in the electrolyte of the present invention include, but are not limited to, N-methoxyethyl trifluoroethyl carbamate, N-methoxyethyl-N-methyl trifluoroethyl carbamate, N-methoxymethyl-N-methyl trifluoroethyl carbamate, N-methoxymethyl trifluoroethyl carbamate, N-methoxymethyl-N-ethyl trifluoroethyl carbamate, N-methoxyethyl-N-ethyl trifluoroethyl carbamate, N-methoxyethyl fluoroethyl carbamate, N-methoxyethyl-N-methyl fluoroethyl carbamate, N-methoxymethyl-N-methyl fluoroethyl carbamate, N-methoxymethyl fluoroethyl carbamate, N-methoxymethyl-N-ethyl fluoroethyl carbamate, N-methoxyethyl-N-ethyl fluoroethyl carbamate, N-methoxyethyl pentafluoropropyl carbamate, N-methoxyethyl-N-methyl pentafluoropropyl carbamate, N-methoxymethyl-N-methyl pentafluoropropyl carbamate, N-methoxymethyl pentafluoropropyl carbamate, N-methoxymethyl-N-ethyl pentafluoropropyl carbamate, N-methoxyethyl-N-ethyl pentafluoropropyl carbamate, N-methoxyethyl hexafluoro-2-propyl carbamate, N-methoxyethyl-N-methyl hexafluoro-2-propyl carbamate, N-methoxymethyl-N-methyl hexafluoro-2-propyl carbamate, N-methoxymethyl hexafluoro-2-propyl carbamate, N-methoxymethyl-N-ethyl hexafluoro-2-propyl carbamate, and N-methoxyethyl-N-ethyl hexafluoro-2-propyl carbamate.

The ionizable lithium salt of the electrolyte according to the present invention may be represented by $Li^+X^-$. The anion of the lithium salt is not particularly limited and may be, for example, $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$ or $(CF_3CF_2SO_2)_2N^-$.

The electrolyte of the present invention can be prepared by suitable methods known in the art. For example, the electrolyte of the present invention may be prepared by mixing the amide compound with the lithium salt at room temperature, then having the mixture react at an appropriate temperature of 70° C. or less, and then purifying the reaction product. Taking into consideration the ionic conductivity and viscosity of the electrolyte, the mixing ratio of the amide compound to the lithium salt is preferably from 1:1 to 8:1, more preferably from 2:1 to 6:1.

There is no particular restriction on the viscosity of the electrolyte according to the present invention. The electrolyte of the present invention preferably has a viscosity of 200 cP or less. Below 200 cP, the electrolyte of the present invention is most suitable for the fabrication of an electrochemical device. The electrolyte of the present invention preferably has an ionic conductivity of 1 to 3 mS/cm. Within this range, the electrolyte is preferably applied to an electrochemical device.

Optionally, the electrolyte of the present invention may further include a carbonate.

Since ionic conductivity of an electrolyte is generally determined depending on the mobility of ions migrating in the electrolyte, factors affecting the ionic conductivity of the electrolyte are the viscosity of the electrolyte and the concentration of ions in the solution. As the viscosity of the solution decreases, migration of ions in the solution becomes easier and the ionic conductivity of the solution increases. As the concentration of ions in the solution increases (i.e. the number of ions as charge carriers increases), the ionic conductivity of the solution increases. The carbonate compound included in the electrolyte of the present invention serves to further lower the viscosity of the electrolyte, resulting in an improvement of ionic conductivity. In view of the foregoing, the viscosity of the electrolyte according to the present invention may be limited to 50 cP or less. The viscosity of the electrolyte is preferably limited to the range of 4 to 30 cP taking the ionic conductivity and thermal stability of the electrolyte into consideration. In view of the same, the ionic, conductivity of the electrolyte according to the present invention is preferably limited to the range of 3 to 6 mS/cm.

In order to attain the viscosity and ionic conductivity ranges defined above, it is preferred that the carbonate compound be included in an amount of 5 to 200 parts by weight, based on 100 parts by weight of the amide compound and the lithium salt.

The carbonate compound may be any of those that are commonly used in non-aqueous electrolytes for lithium secondary batteries. The carbonate compound may be a linear carbonate compound, a cyclic carbonate compound or a mixture thereof. Non-limiting examples of such carbonate compounds include propylene carbonate (PC), ethylene carbonate (EC), diethyl carbonate (DEC), dimethyl carbonate (DMC), dipropyl carbonate (DPC), butylene carbonate, methyl propyl carbonate, ethyl propyl carbonate, ethyl methyl carbonate (EMC). It can be understood that these carbonate compounds may be substituted with at least one halogen atom.

Optionally, the electrolyte of the present invention may further include a linear ester compound. The linear ester compound is much less viscous than the carbonate organic solvent, resulting in a further reduction in the viscosity of the electrolyte and a further improvement in the ionic conductivity of the electrolyte. In addition, the linear ester compound is less reactive with an anode than the carbonate organic solvent. This low reactivity of the linear ester compound suppresses battery swelling and prevents loss of the electrolyte, contributing to a considerable and effective improvement in the charge/discharge characteristics of the electrolyte.

Examples of linear esters suitable for use in the electrolyte of the present invention include methyl acetate, ethyl acetate, methyl propionate, ethyl propionate, propyl propionate and butyl propionate. These linear esters may be used alone or as a mixture of two or more thereof.

It will be apparent to those skilled in the art that various kinds of additives and organic solvents may be further included in the electrolyte of the present invention so long as they do not detract from the objects of the present invention.

The electrolyte of the present invention can be prepared into various forms. For example, the electrolyte of the present invention may be prepared into a liquid electrolyte or a solid or gel polymer electrolyte. The gel polymer electrolyte may be prepared by mixing the electrolyte of the present invention with a polymerizable monomer to obtain a precursor solution, and polymerizing the precursor solution. The polymer electrolyte may be prepared by impregnating a solid or gel polymer with the electrolyte of the present invention.

An explanation will now be given of the gel polymer electrolyte prepared by polymerization of a precursor solution.

First, the electrolyte of the present invention (i) is mixed with (ii) a polymerizable monomer to obtain a precursor solution. Then, the precursor solution is polymerized to prepare the gel polymer electrolyte. It should be understood that the electrolyte may optionally further include a carbonate, as described above.

The kind of monomer is not limited so long as the monomer can be polymerized to prepare the gel polymer, together with the electrolyte. A non-limiting example of the monomer is a vinyl monomer. The vinyl monomer is miscible with the electrolyte and is very simply polymerized to prepare the gel polymer.

Non-limiting examples of vinyl monomers suitable for use in the preparation of the gel polymer include acrylonitrile, methyl methacrylate, methyl acrylate, methacrylonitrile, methylstyrene, vinyl esters, vinyl chloride, vinylidene chloride, acrylamide, tetrafluoroethylene, vinyl acetate, methyl vinyl ketone, ethylene, styrene, p-methoxystyrene and p-cyanostyrene. These vinyl monomers may be used alone or as a mixture of two or more thereof.

The precursor solution may further include a polymerization initiator or a photoinitiator known in the art. The initiator is decomposed by heat or UV light to form a radical. The radical reacts with the monomer ("free-radical polymerization") to prepare the gel polymer electrolyte. The monomer may also be polymerized in the absence of an initiator. Generally, free-radical polymerization involves an initiation reaction in which highly reactive temporary molecules or active sites are formed, a growth reaction in which monomer molecules are added to the active chain ends to form additional active sites at the chain ends, a chain transfer reaction in which the active sites are transferred to the other molecules, and a termination reaction in which centers of the active chains are destroyed.

Non-examples of thermal polymerization initiators suitable for use in the preparation of the gel polymer include: organic peroxides, such as benzoyl peroxide, acetyl peroxide, dilauryl peroxide and di-tert-butyl peroxide; hydroperoxides, such as cumyl hydroperoxide and hydrogen peroxide; azo compounds, such as 2,2-azobis(2-cyanobutane), 2,2-azobis (methylbutyronitrile), azobis(isobutyronitrile) (AIBN) and azobisdimethylvaleronitrile (AMVN); and organometals, such as alkylated silver. Non-limiting examples of photoinitiators capable of forming radicals by light (e.g., UV light) include chloroacetophenone, diethoxyacetophenone (DEAP), 1-phenyl-2-hydroxy-2-methyl propanone (HMPP), 1-hydroxycyclohexyl phenyl ketone, α-aminoacetophenone, benzoin ether, benzyl dimethyl ketal, benzophenone, thioxanthone and 2-ethylanthraquinone (2-ETAQ).

In addition to the components described above, the precursor solution may optionally further contain other additives known in the art.

The gel polymer electrolyte can be prepared from the precursor solution by a suitable method known in the art. The gel polymer electrolyte is preferably prepared by in-situ polymerization inside an electrochemical device. The in-situ polymerization can be carried out by heating or UV irradiation. It is preferable to adjust the weight ratio of the electrolyte to the monomer in the precursor solution to 0.5-0.95:0.05-0.5. The degree of polymerization of the gel polymer may vary depending on a reaction factor, such as polymerization time, polymerization temperature or the amount of light irradiated. Thus, the degree of polymerization is controlled such that the polymer does not shrink by excessive polymerization without leakage of the electrolyte.

Alternatively, the polymer electrolyte may be prepared by injecting the electrolyte into a solid or gel polymer, which is previously prepared before injection, to allow the electrolyte to be impregnated into the polymer.

Non-limiting examples of polymers suitable for use in the preparation of the polymer electrolyte include polymethyl methacrylate, polyvinylidene difluoride, polyvinyl chloride, polyethylene oxide and polyhydroxyethyl methacrylate. These polymers may be used alone or as a mixture of two or more thereof. This method may be simpler to implement than the method based on in-situ polymerization.

Alternatively, the polymer electrolyte may be prepared by dissolving a polymer and the electrolyte in a solvent and removing the solvent. In this case, the electrolyte is contained inside the polymer matrix.

The solvent is not particularly limited, and non-limiting examples thereof include toluene, acetone, acetonitrile and THF. There is no particular restriction on the removal method of the solvent. For example, the solvent may be removed by heating.

The electrolyte of the present invention can be applied to electrochemical devices commonly known in the art that require various electrochemical properties, depending on the intended application and purpose.

Non-limiting examples of such electrochemical devices include all kinds of primary and secondary batteries, fuel cells, solar cells, electrochromic devices, electrolytic condensers and capacitors, more specifically, lithium secondary batteries, electric double-layer capacitors, dye-sensitized solar cells and electrochromic devices.

Specifically, a lithium secondary battery employing the electrolyte of the present invention has good thermal stability. As an example, a pouch-type lithium secondary battery employing the electrolyte of the present invention may have a thickness variation no greater than 10% even after being charged up to 4.2 V at 90° C. for 4 hr.

MODE FOR INVENTION

Hereinafter, the present invention will be explained in detail with reference to embodiments. The embodiments of the present invention, however, may take several other forms, and the scope of the invention should not be construed as being limited to the following examples. The embodiments of the present invention are provided to more fully explain the present invention to those having ordinary knowledge in the art to which the present invention pertains.

EXAMPLES

Example 1

6.8 g of N-methoxyethyl-N-methyl trifluoroethyl carbamate and 2 g of $LiPF_6$ were placed in a round-bottom flask and slowly stirred under a nitrogen atmosphere for 2 hr, obtaining 8.8 g of an electrolyte.

Example 2

5.2 g of N-methoxyethyl-N-methyl fluoroethyl carbamate and 2 g of $LiPF_6$ were placed in a round-bottom flask and slowly stirred under a nitrogen atmosphere for 2 hr, obtaining 7.2 g of an electrolyte.

Example 3

7.5 g of N-methoxymethyl-N-ethyl trifluoroethyl carbamate and 2 g of LiPF$_6$ were placed in a round-bottom flask and slowly stirred under a nitrogen atmosphere for 2 hr, obtaining 9.3 g of an electrolyte.

Example 4

6.5 g of N-methoxyethyl-N-methyl trifluoroethyl carbamate and 2 g of LiPF$_6$ were placed in a round-bottom flask and slowly stirred under a nitrogen atmosphere for 2 hr. 1.7 g of ethyl methyl carbonate was added to the mixture, obtaining 10.1 g of an electrolyte.

Example 5

4.4 g of N-methoxyethyl-N-methyl fluoroethyl carbamate and 2 g of LiPF$_6$ were placed in a round-bottom flask and slowly stirred under a nitrogen atmosphere for 2 hr. 1.6 g of ethyl methyl carbonate was added to the mixture, obtaining 7.8 g of an electrolyte.

Example 6

7.5 g of N-methoxymethyl-N-ethyl trifluoroethyl carbamate and 2 g of LiPF$_6$ were placed in a round-bottom flask and slowly stirred under a nitrogen atmosphere for 2 hr. 1.6 g of ethyl methyl carbonate was added to the mixture, obtaining 10.9 g of an electrolyte.

Example 7

4.125 g of N-methoxyethyl-N-methyl trifluoroethyl carbamate, 2.25 g of ethylene carbonate, 1.125 g of ethyl propionate and 2 g of LiPF$_6$ were placed in a round-bottom flask and slowly stirred under a nitrogen atmosphere for 2 hr, obtaining 9.5 g of an electrolyte.

Example 8

4.125 g of N-methoxyethyl-N-methyl fluoroethyl carbamate, 2.25 g of ethylene carbonate, 1.125 g of ethyl propionate and 2 g of LiPF$_6$ were placed in a round-bottom flask and slowly stirred under a nitrogen atmosphere for 2 hr, obtaining 9.5 g of an electrolyte.

Comparative Example 1

4.7 g of purified ethyl carbamate and 6 g of LiTFSI were placed in a round-bottom flask and slowly stirred under a nitrogen atmosphere at room temperature for 2 hr, obtaining 10.7 g of an electrolyte.

Comparative Example 2

6.2 g of N-methoxyethyl-N-methyl methyl carbamate and 2 g of LiPF$_6$ were placed in a round-bottom flask and slowly stirred under a nitrogen atmosphere at room temperature for 2 hr, obtaining 8.2 g of an electrolyte.

Comparative Example 3

4.7 g of purified methyl carbamate and 6 g of LiTFSI were placed in a round-bottom flask and slowly stirred under a nitrogen atmosphere for 2 hr, obtaining 10.7 g of an electrolyte.

Comparative Example 4

5 g of N-methoxy-N-methylamine salt was dissolved in water. The solution was adjusted to a basic pH with an aqueous NaHCO$_3$ solution at a low temperature, and then 5.6 g of ethyl chloroformate was slowly added dropwise thereto. After completion of the reaction, the reaction mixture was extracted with ethyl acetate. Distillation of the extract yielded N-methoxy-N-methyl ethyl carbamate.

5.8 g of the N-methoxy-N-methyl ethyl carbamate and 2 g of LiPF$_6$ were placed in a round-bottom flask and slowly stirred under a nitrogen atmosphere for 2 hr, obtaining about 7.6 g of an electrolyte.

Comparative Example 5

4.5 g of N-methoxy-N-methyl 2,2,2-trifluoroethyl carbamate and 2 g of LiPF$_6$ were placed in a round-bottom flask and slowly stirred under a nitrogen atmosphere for 2 hr. 1.7 g of ethyl methyl carbonate was added to the mixture, obtaining about 8.1 g of an electrolyte.

Comparative Example 6

3.4 g of N-methoxy-N-methyl 2-fluoroethyl carbamate and 2 g of LiPF$_6$ were placed in a round-bottom flask and slowly stirred under a nitrogen atmosphere for 2 hr. 1.6 g of ethyl methyl carbonate was added to the mixture, obtaining about 6.8 g of an electrolyte.

Experimental Example 1

Evaluation of Physical Properties of the Electrolytes

The physical properties of the electrolytes prepared in Examples 1-8 and Comparative Examples 1-6 were evaluated as follows.

The viscosities of the electrolytes were measured using a viscometer (RS150) at 25° C. The conductivities of the electrolytes were measured using Inolab 740. The results are shown in Table 1.

TABLE 1

|  | Viscosity (cP) | Conductivity (mS/cm) | Electrochemical window (V) |
| --- | --- | --- | --- |
| Example 1 | 25 | 1.6 | 0.45-4.9 |
| Example 2 | 23 | 1.5 | 0.45-4.85 |
| Example 3 | 19.5 | 1.7 | 0.45-4.9 |
| Example 4 | 9.6 | 4.2 | 0.45-4.9 |
| Example 5 | 7.8 | 5.1 | 0.45-4.85 |
| Example 6 | 8.2 | 4.7 | 0.45-4.9 |
| Example 7 | 9.7 | 4.17 | 0.45-4.9 |
| Example 8 | 10.2 | 3.5 | 0.45-4.85 |
| Comparative Example 1 | 65 | 1.4 | 0.6-4.5 |
| Comparative Example 2 | 29 | 1.5 | 0.45-4.5 |
| Comparative Example 3 | 62.0 | 1.7 | 0.6-4.7 |
| Comparative Example 4 | 7.3 | 4.05 | 0.7-4.5 |
| Comparative Example 5 | 12 | 3.79 | 0.45-4.75 |
| Comparative Example 6 | 10.5 | 4.3 | 0.4-4.68 |

As shown from the results in Table 1, the inventive electrolytes showed better results in terms of viscosity and ionic conductivity than the comparative electrolytes. In addition, the inventive electrolytes had wider electrochemical windows, particularly higher upper limits (oxidation potentials) thereof, than the comparative electrolytes.

Particularly, the amide compound included in each of the inventive electrolytes has an amine group substituted with at least one alkoxyalkyl group (corresponding to at least one of $R_1$ and $R_2$ bonded to the N atom in Formula 1) and includes at least one halogen atom. The upper limits of the electrochemical windows of the inventive electrolytes of Examples 1-8 were approximately 10% higher than the upper limit of the electrochemical window of the electrolyte of Comparative Example 4, which includes the amide compound having an alkoxy group as a substituent bonded to the N atom of the amine group and not being halogenated.

Further, the electrolytes of Examples 4 and 5 had lower viscosities, higher ionic conductivities and higher upper limits of electrochemical windows than the electrolytes of Comparative Examples and 6, each of which includes the amide compound having an alkyl group as a substituent bonded to the N atom of the amine group and including halogen atoms. These results indicate that the electrolytes of Examples 4 and 5 had better performance.

Fabrication of Batteries

Example 9

Production of Cathode $LiCoO_2$ as a cathode active material, artificial graphite as a conductive material and polyvinylidene fluoride as a binder were mixed in a weight ratio of 94:3:3, and N-methylpyrrolidone was added thereto to prepare a slurry. The slurry was applied to an aluminum foil and dried at 130° C. for 2 hr to produce a cathode.

(Production of Anode)

Artificial graphite as an anode active material, a conductive material and a binder were mixed in a weight ratio of 94:3:3, and N-methylpyrrolidone was added thereto to prepare a slurry. The slurry was applied to a copper foil and dried at 130° C. for 2 hr to produce an anode.

(Fabrication of Secondary Batteries)

The cathode and the anode were cut to sizes of 1 $cm^2$, and a separator was interposed therebetween. The electrolyte of Example 1 was injected into the electrode assembly, completing the fabrication of a secondary battery illustrated in FIG. 1. Reference numerals 1, 2, 3, 4, 5, 6 and 7 in FIG. 1 designate the cathode, the anode, the separator, the electrolyte, a spacer, a coin can container, a coin can cover, and a sealing rubber.

Example 10

A secondary battery was fabricated in the same manner as in Example 9, except that the electrolyte of Example 4 was used.

Comparative Example 7

A secondary battery was fabricated in the same manner as in Example 9, except that a 1 M solution of $LiPF_6$ in ethylene carbonate and ethyl methyl carbonate (1:2, v/v) was used as an electrolyte.

Comparative Example 8

A secondary battery was fabricated in the same manner as in Example 9, except that the electrolyte of Comparative Example 1 was used.

Comparative Example 9

A secondary battery was fabricated in the same manner as in Example 10, except that a 1 M solution of $LiPF_6$ in ethylene carbonate and ethyl methyl carbonate (1:2, v/v) was used as an electrolyte.

Comparative Example 10

A secondary battery was fabricated in the same manner as in Example 10, except that the electrolyte of Comparative Example 2 was used.

Experimental Example 2

Evaluation of Roam-Temperature Performance of the Secondary Batteries

Each of the secondary batteries fabricated in Example 9 and Comparative Example 7 was charged/discharged at 0.5 $mAcm^{-2}$ at room temperature. The discharge capacity and charge/discharge efficiency of the battery were measured proceeding the charge/discharge cycles. The results are shown in FIG. 2.

Figure 2:
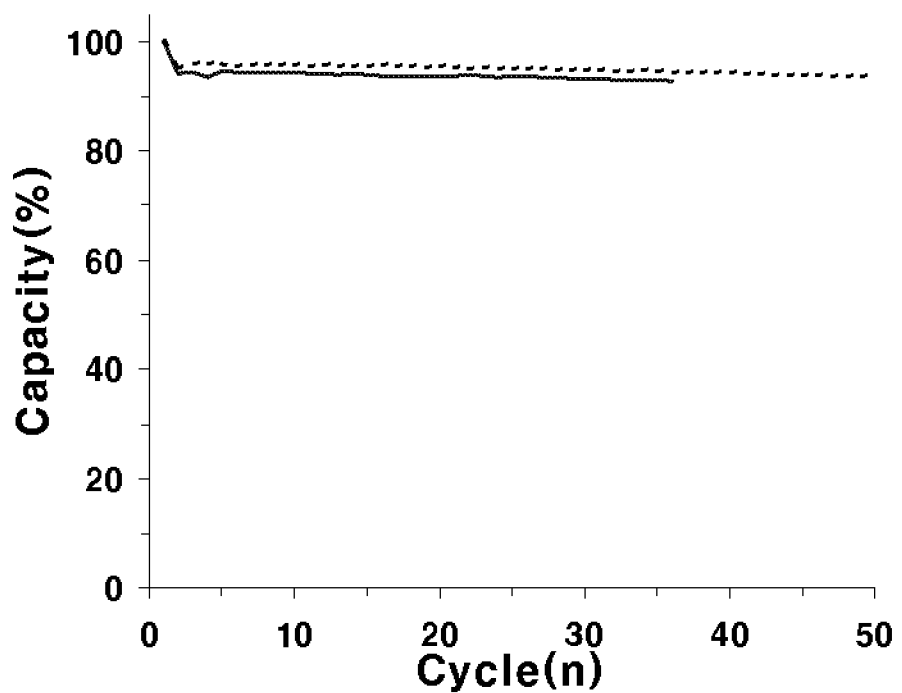
FIG. 2 is a graph showing the charge/discharge efficiencies of secondary batteries fabricated in Example 9 (solid curve) and Comparative Example 7 (dashed curve)

The results reveal that the battery of Comparative Example 7 using the electrolyte including the general carbonate solvents and the battery of Example 9 using the inventive electrolyte had discharge capacities of at least 90% and charge/discharge efficiencies of 98% after 30 cycles of charging/discharging, as shown in FIG. 2. The solid and dashed curves in FIG. 2 show the capacities of the batteries of Example 9 and Comparative Example 7, respectively. From these results, it can be confirmed that the performance of the inventive electrolyte at room temperature is comparable to that of the commercially available liquid electrolyte.

Experimental Example 3

High Temperature Storage Tests of the Secondary Batteries

The secondary batteries of Example 9 and Comparative Example 8 were charged at 0.5 $mAcm^{-2}$ and were allowed to stand at 90° C. for 4 hr. The thicknesses of the batteries before and after standing were measured. The results are shown in Table 2.

TABLE 2

|  | Initial thickness (mm) | Final thickness (mm) | Increment (%) |
| --- | --- | --- | --- |
| Example 9 | 3.86 | 4.20 | 9.0 |
| Comparative Example 8 | 3.85 | 4.43 | 15.0 |

The results in Table 2 demonstrate that the battery of Example 9 using the inventive electrolyte were more stable at a high temperature than that of Comparative Example 8 using the conventional electrolyte.

Experimental Example 4

Evaluation of High-Temperature Performance of the Secondary Batteries

After each of the secondary batteries of Example 10 and Comparative Examples 9-10 were charged/discharged at 0.5 mAcm$^{-2}$ at 45° C., the charge/discharge efficiency of the battery was measured with increasing number of cycles. The results are shown in FIG. 3.

Figure 3:
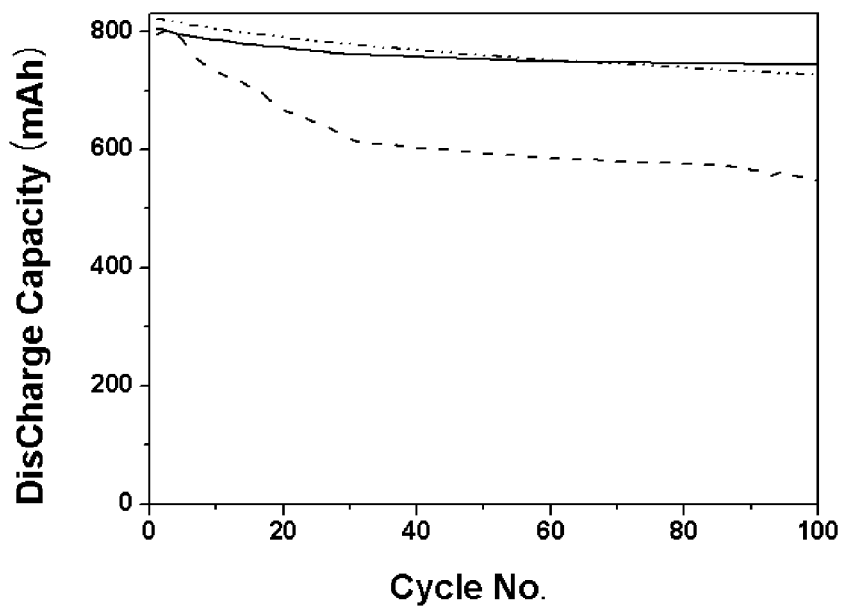
FIG. 3 is a graph showing the charge/discharge efficiencies of secondary batteries fabricated in Example 10 (solid curve), Comparative Example 9 (dashed curve) and Comparative Example 10 (alternate long and two short dashed curve) at a high temperature.

The graph of FIG. 3 shows that after 100 cycles of charging/discharging, each of the secondary batteries of Example 10 and Comparative Example 10 had a discharge capacity of at least 90% compared to the initial capacity and a charge/discharge efficiency of 98%. In contrast, the secondary battery of Comparative Example 9 had a discharge capacity of 68%.

In FIG. 3, the solid curve represents the discharge capacities of the battery of Example 10, the dashed curve represents the discharge capacities of the battery of Comparative Example 9, and the alternate long and two short dashed curve represents. the discharge capacities of the battery of Comparative Example 10. From the graph of FIG. 3, it can be confirmed that the room-temperature performance of the inventive electrolyte is comparable to that of the commercially available liquid electrolyte.

Experimental Example 5

Impedance Measurement of the Secondary Batteries

Figure 4:
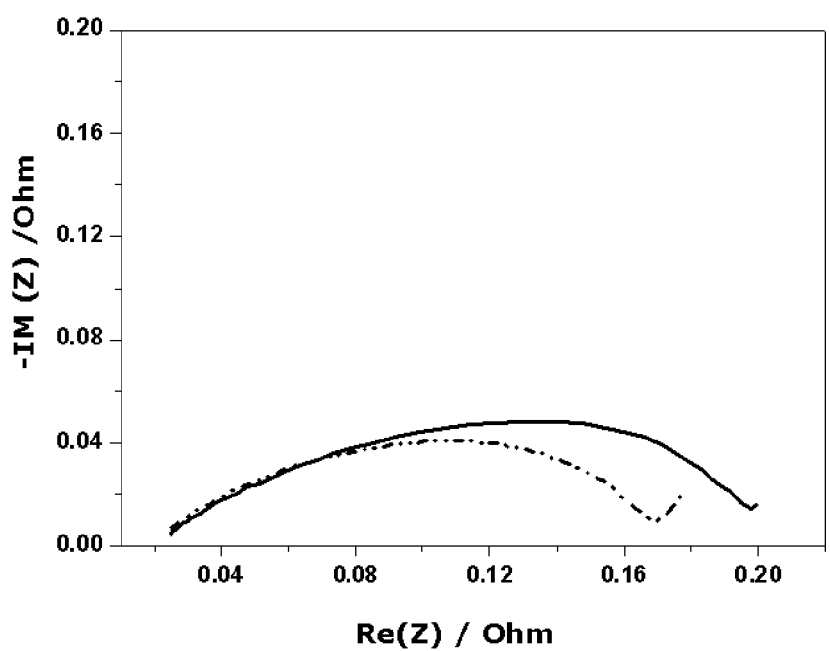
FIG. 4 is a graph showing the impedances of secondary batteries fabricated in Example 10 (alternate long and two short dashed curve) and Comparative Example 9 (solid curve).

The impedances of the batteries of Example 10 and Comparative Example 9 were measured using a potentiostat. The results are shown in FIG. 4. After each of the batteries was charged to 4.2 V, a low voltage of 10 mV was applied thereto with increasing frequency from 3 kHz to 100 mHz. The resulting current responses were measured to determine the impedances of the battery.

In FIG. 4, the alternate long and two short dashed curve represents the impedances of the battery of Example 10 and the solid curve represents the impedances of the battery of Comparative Example 9.

The present invention has been described in detail. However, it should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. An electrolyte comprising an amide compound and an ionizable lithium salt wherein the amide compound has an amine group substituted with at least one alkoxyalkyl group and comprises at least one halogen atom, represented by Formula 1:

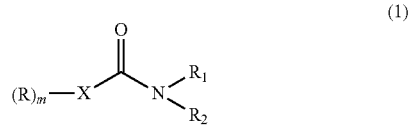

(1)

wherein R is selected from the group consisting of $C_1$-$C_{20}$ halogenated alkyl groups, halogenated alkylamine groups, halogenated alkenyl groups and halogenated aryl groups, $R_1$ and $R_2$ are each independently selected from the group consisting of hydrogen, halogen, $C_1$-$C_{20}$ alkyl groups, alkylamine groups, alkenyl groups and aryl groups, with the proviso that at least one of $R_1$ and $R_2$ is an alkoxyalkyl group represented by $CH_3$—$(CH_2)_p$—$O(CH_2)_q$—, p being an integer from 0 to 8 and q being an integer from 1 to 8, and X is selected from the group consisting of silicon, oxygen, phosphorus, sulfur and hydrogen, provided that i) when X is hydrogen, m is 0, ii) when X is oxygen or sulfur, m is 1, iii) when X is nitrogen or phosphorus, m is 2, and iv) when X is silicon, m is 3.

2. The electrolyte according to claim 1, wherein the amide compound is selected from the group consisting of N-methoxyethyl trifluoroethyl carbamate, N-methoxyethyl-N-methyl trifluoroethyl carbamate, N-methoxymethyl-N-methyl trifluoroethyl carbamate, N-methoxymethyl trifluoroethyl carbamate, N-methoxymethyl-N-ethyl trifluoroethyl carbamate, N-methoxyethyl-N-ethyl trifluoroethyl carbamate, N-methoxyethyl fluoroethyl carbamate, N-methoxyethyl-N-methyl fluoroethyl carbamate, N-methoxymethyl-N-methyl fluoroethyl carbamate, N-methoxymethyl fluoroethyl carbamate, N-methoxymethyl-N-ethyl fluoroethyl carbamate, N-methoxyethyl-N-ethyl fluoroethyl carbamate, N-methoxyethyl pentafluoropropyl carbamate, N-methoxyethyl-N-methyl pentafluoropropyl carbamate, N-methoxymethyl-N-methyl pentafluoropropyl carbamate, N-methoxymethyl pentafluoropropyl carbamate, N-methoxymethyl-N-ethyl pentafluoropropyl carbamate, N-methoxyethyl-N-ethyl pentafluoropropyl carbamate, N-methoxyethyl hexafluoro-2-propyl carbamate, N-methoxyethyl-N-methyl hexafluoro-2-propyl carbamate, N-methoxymethyl-N-methyl hexafluoro-2-propyl carbamate, N-methoxymethyl hexafluoro-2-propyl carbamate, N-methoxymethyl-N-ethyl hexafluoro-2-propyl carbamate and N-methoxyethyl-N-ethyl hexafluoro-2-propyl carbamate.

3. The electrolyte according to claim 1, wherein the anion of the lithium salt is selected from the group consisting of F$^-$, Cl$^-$, Br$^-$, I$^-$, NO$_3^-$, N(CN)$_2^-$, BF$_4^-$, ClO$_4^-$, PF$_6^-$, (CF$_3$)$_2$PF$_4^-$, (CF$_3$)$_3$PF$_3^-$, (CF$_3$)$_4$PF$_2^-$, (CF$_3$)$_5$PF$^-$, (CF$_3$)$_6$P$^-$, CF$_3$SO$_3^-$, CF$_3$CF$_2$SO$_3^-$, (CF$_3$SO$_2$)$_2$N$^-$, (FSO$_2$)$_2$N$^-$, CF$_3$CF$_2$(CF$_3$)$_2$CO$^-$, (CF$_3$SO$_2$)$_2$CH$^-$, (SF$_5$)$_3$C$^-$, (CF$_3$SO$_2$)$_3$C$^-$, CF$_3$(CF$_2$)$_7$SO$_3^-$, CF$_3$CO$_2^-$, CH$_3$CO$_2^-$, SCN$^-$ and (CF$_3$CF$_2$SO$_2$)$_2$N$^-$.

4. The electrolyte according to claim 1, wherein the amide compound and the lithium salt are present in a molar ratio of 1-8:1.

5. The electrolyte according to claim 1, wherein the electrolyte has an electrochemical window of 0.4 to 5.0 V.

6. The electrolyte according to claim 1, wherein the electrolyte has a viscosity of 200 cP or less.

7. The electrolyte according to claim 1, wherein the electrolyte has an ionic conductivity of 1 to 3 mS/cm.

8. The electrolyte according to claim 1, further comprising a carbonate compound.

9. The electrolyte according to claim 8, wherein the carbonate compound is selected from the group consisting of linear carbonates, cyclic carbonates and mixtures thereof.

10. The electrolyte according to claim 9, wherein the electrolyte has an ionic conductivity of 3 to 6 mS/cm.

11. The electrolyte according to claim 8, wherein the carbonate compound is selected from the group consisting of propylene carbonate (PC), ethylene carbonate (EC), diethyl carbonate (DEC), dimethyl carbonate (DMC), dipropyl carbonate (DPC), butylene carbonate, methyl propyl carbonate, ethyl propyl carbonate, ethyl methyl carbonate (EMC), and mixtures thereof.

12. The electrolyte according to claim 8, wherein the carbonate compound is present in an amount of 5 to 200 parts by weight, based on 100 parts by weight of the amide compound and the lithium salt.

13. The electrolyte according to claim 8, wherein the electrolyte has a viscosity of 50 cP or less.

14. The electrolyte according to claim 13, wherein the electrolyte has a viscosity of 4 to 30 cP.

15. The electrolyte according to claim 1, further comprising a linear ester.

16. The electrolyte according to claim 15, wherein the linear ester is selected from the group consisting of methyl propionate, ethyl propionate, propyl propionate, butyl propionate, and mixtures thereof.

17. The electrolyte according to claim 1, wherein the electrolyte is mixed with a polymerizable monomer to obtain a precursor solution, followed by polymerization of the precursor solution to prepare a gel polymer electrolyte.

18. The electrolyte according to claim 1, wherein the electrolyte is impregnated into a polymer to prepare a polymer electrolyte.

19. An electrochemical device comprising a cathode, an anode and the electrolyte according to claim 1.

20. The electrochemical device according to claim 19, wherein the electrochemical device is a lithium secondary battery.

21. The electrochemical device according to claim 20, wherein the lithium secondary battery is a pouch type secondary battery that has a thickness variation no greater than 10% after being charged to 4.2 V at 90° C. for 4 hr.

* * * * *